(12) United States Patent
Lynch et al.

(10) Patent No.: US 9,824,236 B2
(45) Date of Patent: Nov. 21, 2017

(54) SYSTEM FOR ANONYMIZING AND AGGREGATING PROTECTED INFORMATION

(71) Applicant: Accenture Global Services Limited, Dublin (IE)

(72) Inventors: Cecil O'Dell Lynch, Granite Bay, CA (US); Dennis James Carroll, Leander, TX (US); Andrew John Truscott, Spring, TX (US); German Acuna, Austin, TX (US)

(73) Assignee: ACCENTURE GLOBAL SERVICES LIMITED, Dublin (IE)

(*) Notice: Subject to any disclaimer, the term of this patent is extended or adjusted under 35 U.S.C. 154(b) by 212 days.

(21) Appl. No.: 14/716,154

(22) Filed: May 19, 2015

(65) Prior Publication Data
US 2016/0342812 A1   Nov. 24, 2016

(51) Int. Cl.
*G06F 21/62* (2013.01)
*H04L 29/06* (2006.01)
(Continued)

(52) U.S. Cl.
CPC .... *G06F 21/6254* (2013.01); *G06F 17/30598* (2013.01); *G06F 17/30604* (2013.01);
(Continued)

(58) Field of Classification Search
CPC ... G06F 21/6254; G06F 19/322; H04L 9/3242
See application file for complete search history.

(56) References Cited

U.S. PATENT DOCUMENTS

| 6,397,224 B1 | 5/2002 | Zubeldia et al. |
| 7,668,820 B2 | 2/2010 | Zuleba |
| (Continued) | | |

FOREIGN PATENT DOCUMENTS

| WO | 9855977 A1 | 12/1998 |
| WO | 2012166633 A1 | 12/2012 |

OTHER PUBLICATIONS

Extended European Search Report for EP 14194259.9, Completed Jun. 30, 2015.
(Continued)

*Primary Examiner* — Anthony Brown
*Assistant Examiner* — Samuel Ambaye
(74) *Attorney, Agent, or Firm* — Brinks Gilson & Lione

(57) ABSTRACT

A system for anonymizing and aggregating protected information (PI) from a plurality of data sources includes a master index server coupled to a data repository. The master index server receives an anonymized records associated with an individual from a plurality of data hashing appliances. The system includes a cluster matching engine that applies a plurality of rules to hashed data elements of the received record for comparing hashed data elements of the record with hashed data elements of a plurality of clusters of anonymized records associated with different individuals stored in the data repository to determine whether the individual associated with the received record corresponds to an individual associated with one of the clusters of anonymized records. When a match is found, the cluster matching engine adds the received record to the cluster of anonymized records associated with that individual.

18 Claims, 9 Drawing Sheets

(51) Int. Cl.
*H04W 12/02* (2009.01)
*G06F 17/30* (2006.01)
*G06F 19/00* (2011.01)
*H04L 9/32* (2006.01)

(52) U.S. Cl.
CPC .......... *G06F 19/322* (2013.01); *H04L 9/3242* (2013.01); *H04L 63/0407* (2013.01); *H04L 63/0421* (2013.01); *H04W 12/02* (2013.01); *H04L 2209/24* (2013.01); *H04L 2209/42* (2013.01)

(56) References Cited

U.S. PATENT DOCUMENTS

| | | | |
|---|---|---|---|
| 7,865,376 | B2 | 1/2011 | Ober et al. |
| 8,275,850 | B2 | 9/2012 | Kohan et al. |
| 2002/0073099 | A1* | 6/2002 | Gilbert ................ G06F 17/3061 |
| 2002/0073138 | A1 | 6/2002 | Gilbert et al. |
| 2003/0187713 | A1 | 10/2003 | Hood |
| 2004/0025057 | A1 | 2/2004 | Cook |
| 2004/0107205 | A1 | 6/2004 | Burdick et al. |
| 2005/0236474 | A1 | 10/2005 | Onuma et al. |
| 2005/0256741 | A1 | 11/2005 | Kohan et al. |
| 2006/0020611 | A1 | 1/2006 | Gilbert et al. |
| 2006/0147083 | A1* | 7/2006 | Piersol .................... G06F 21/16 382/100 |
| 2007/0192139 | A1 | 8/2007 | Cookson et al. |
| 2008/0240425 | A1 | 10/2008 | Rosales et al. |
| 2011/0010563 | A1* | 1/2011 | Lee .................... G06F 21/6254 713/189 |
| 2012/0303616 | A1* | 11/2012 | Abuelsaad .......... G06F 21/6227 707/736 |

OTHER PUBLICATIONS

First Examination report for Australian Application No. 2014265125, dated Dec. 23, 2014.
Second Examination report for Australian Application No. 2014265125, dated May 21, 2015.
First Examination report for Australian Application No. 2015275323, dated Oct. 27, 2016.
Extended European Search Report for 16 170 098.4, Completed Jul. 11, 2016.
First Examination report for Australian Application No. 2016202995, dated Aug. 1, 2017.

* cited by examiner

| Rule # | MNR/Source | SSN | gender | byyear | bdate | LN | FN | MN | addr | city | state | zip | phone | count | result |
|---|---|---|---|---|---|---|---|---|---|---|---|---|---|---|---|
| 1 | 1 | x | x | x | x | x | x | x | x | x | x | x | x | 0 | 1 |
| 2 | 0 | 1 | x | x | x | x | x | x | x | x | x | x | x | 0 | 1 |
| 3 | 0 | x | 1 | 1 | 1 | 1 | 0 | 0 | 1 | 1 | 1 | 1 | 1 | 0 | 0 |
| 4 | 0 | x | 0 | x | x | x | x | x | x | x | x | x | x | 0 | 0 |
| 5 | 0 | 4 | 1 | 1 | 1 | 1 | 1 | x | x | x | x | x | x | 0 | 1 |
| 6 | 0 | 4 | 1 | 2 | 2 | 2 | 2 | 2 | 2 | 2 | 2 | 2 | 2 | 8 | 1 |

Fig. 4

SYSTEM FOR ANONYMIZING AND AGGREGATING PROTECTED INFORMATION

BACKGROUND OF THE INVENTION

1. Technical Field

This disclosure relates to aggregating records, and in particular, to aggregating and organizing records that include protected/confidential information in a manner that protects the identity of the individual associated with the record.

2. Background

Confidential records are increasingly becoming digitized and stored in computer databases. Data privacy and security issues are thus paramount, as well as compliance with applicable laws and regulations. For example, in the United States, the HIPAA (Health Insurance Portability And Accountability Act) requires that patient medical records be kept confidential, and not released to third parties without authorization. Yet, it is advantageous for different entities to have access to certain medical records for purposes of research, clinical studies, and diagnosis. However, many regulations, including HIPAA, do not permit unrelated or independent entities to aggregate medical records as such aggregation could permit the entity to identify persons associated with the medical records, resulting in a privacy breach.

Further, even when confidential records are properly obtained, such records may be incomplete, erroneous, and/or ambiguous. For example, a health insurance company may receive claims from two different medical offices where the patient's name is spelled differently. Thus, aggregating and associating confidential records corresponding to a particular patient is difficult, irrespective of the privacy and compliance issues.

Accordingly, a need exists to allow analysis of information in confidential records in a protected (i.e., anonymous) fashion by aggregating and identifying the records as belonging to a common individual without revealing the identity of the individual. In the context of medical records, this is useful in research, clinical studies, or when identifying medical conditions, particularly when such patient medical records are obtained from unrelated databases or source systems.

SUMMARY

In one aspect, a system for anonymizing and aggregating protected information (PI) from a plurality of data sources is provided. The system includes a master index server coupled to a data repository. The master index server is configured to receive an anonymized record associated with an individual from a plurality of data hashing appliances. The system includes a cluster matching engine operatively coupled to the master index server and the data repository configured to apply a plurality of rules to hashed data elements of the received anonymized record for comparing hashed data elements of the received anonymized patient medical record with hashed data elements of clusters of anonymized records stored in the data repository, each record in a given cluster of anonymized records having been previously determined to be associated with a same individual and being associated with a unique cluster identifier, to determine whether an individual associated with the received anonymized record corresponds to one of the individuals associated with a cluster of anonymized records. When the received anonymized record is determined to correspond to an individual associated with a cluster of anonymized records, the cluster matching engine is configured to add the received anonymized record to the cluster of anonymized records associated with that individual.

In a second aspect, a method for anonymizing and aggregating protected information (PI) from multiple data sources is provided. The method includes receiving, by a master index server coupled to a data repository, an anonymized record associated with an individual from a plurality of data hashing appliances. The method further includes applying, by a cluster matching engine operatively coupled to the master index server and the data repository, a plurality of rules to hashed data elements of the received anonymized record for comparing hashed data elements of the received anonymized record with hashed data elements of a plurality of clusters of anonymized records associated with an individual stored in the data repository, each record in a given cluster of anonymized records having been previously determined to be associated with a same individual and being associated with a unique cluster identifier, to determine whether the individual associated with the received anonymized record corresponds to one of the individuals associated with a cluster of anonymized records. When the received anonymized record is determined to correspond to the an individual associated with one of the clusters of anonymized records, the method includes adding the received anonymized record to the cluster of anonymized records associated with that individual.

In a third aspect, a non-transitory computer readable medium is provided for storing instruction code for anonymizing and aggregating protected information (PI) from multiple data sources. The instruction code is executable by a machine for causing the machine to receive an anonymized record associated with an individual from a plurality of data hashing appliances. The instruction code also causes the machine to apply a plurality of rules to hashed data elements of the received anonymized record for comparing hashed data elements of the received anonymized record with hashed data elements of a plurality of clusters of anonymized records stored in a data repository, each record in a given cluster of anonymized records having been previously determined to be associated with a same individual and being associated with a unique cluster identifier, to determine whether the individual associated with the received anonymized record corresponds to one of the individuals associated with a cluster of anonymized records. When the received anonymized record is determined to correspond to an individual associated with a cluster of anonymized records, the instruction code causes the machine to add the received anonymized record to the cluster of anonymized patient medical records associated with that individual.

Using the system for anonymizing and aggregating protected information, research can be done retrospectively across a broad population with more complete information on each individual while still maintaining confidentiality of the individual and complying with various regulations, such as HIPAA.

Other embodiments of the systems, methods, features, and their corresponding advantages will be, or will become, apparent to one with skill in the art upon examination of the following figures and detailed description. It is intended that all such additional systems, methods, features, and advantages be included within this description, be within the scope of the invention, and be protected by the following claims.

BRIEF DESCRIPTION OF THE DRAWINGS

The described system for anonymizing and aggregating protected information (PI) may be better understood with reference to the following drawings and the description. The components in the figures are not necessarily to scale, emphasis instead being placed upon illustrating the principles of the invention. Moreover, in the figures, like reference numerals designate corresponding parts throughout the different views.

FIG. 4 illustrates an exemplary rules table that includes control values for controlling the comparison operation of the comparison engine.

DETAILED DESCRIPTION OF THE PREFERRED EMBODIMENTS

The embodiments and figures disclose a system and method for aggregating and anonymizing protected information in the form of patient medical records. However, the embodiments may be adapted to work with other types of records for which privacy is of concern.

Figure 1:
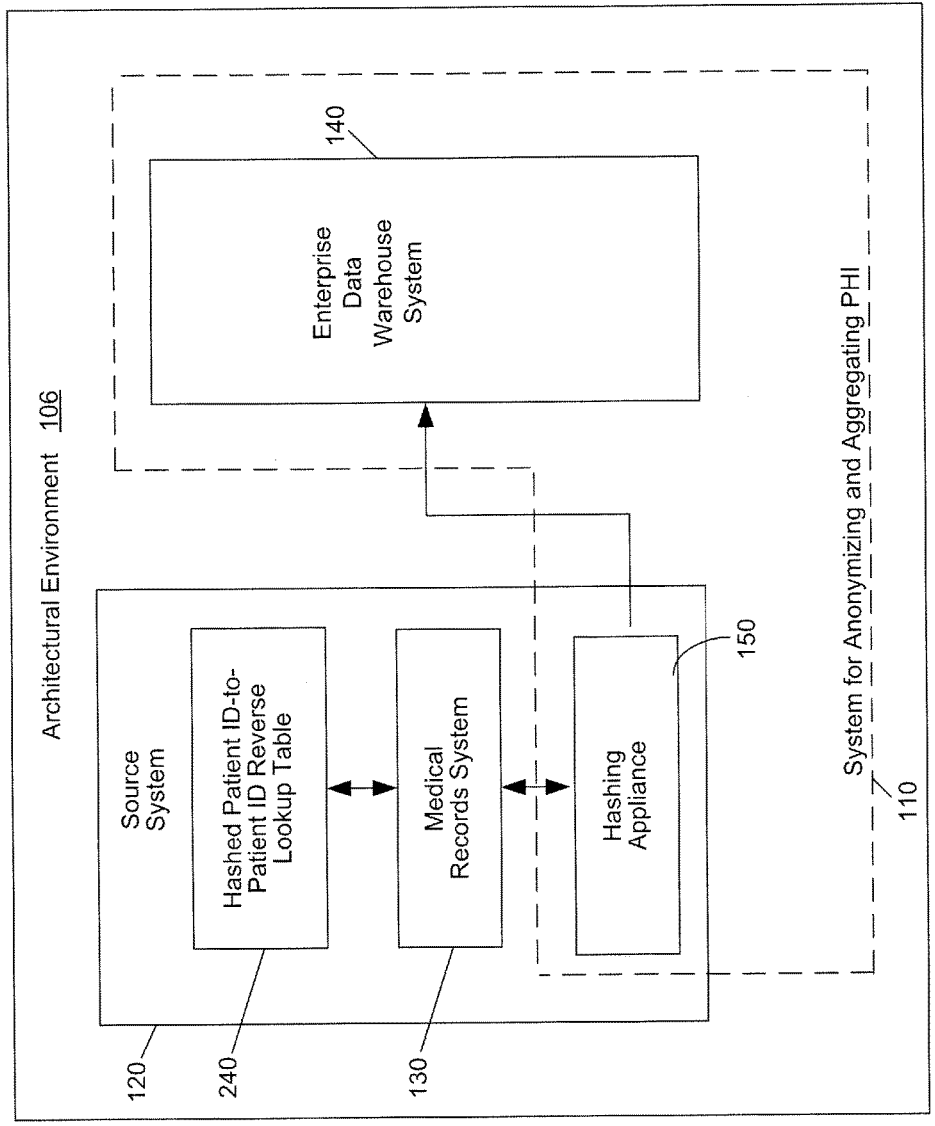
FIG. 1 is a block diagram of an environment in which a system for anonymizing and aggregating protected health information may operate, according to a specific embodiment.

FIG. 1 is a high-level hardware block diagram of an architectural environment in which a system for anonymizing and aggregating protected health information 110 may operate. The architectural environment 100 may include a plurality of source systems 120, each of which may include a plurality of medical records systems 130. The architectural environment 100 may also include an enterprise data warehouse system 140 operatively coupled to one or more source systems 120. The system for anonymizing and aggregating protected health information (PHI) 110 may functionally include the enterprise data warehouse system 140, and may also include an anonymizer hashing appliance 150 embedded in the source system 120. However, the placement of each component within the overall architectural environment 100 may vary to include additional components or fewer components, depending on the specific embodiment. Note that the phrase "protected health information" may be used interchangeably with the phrase "patient health information," and may be broader in scope than may be used or explicitly defined per HIPAA.

Figure 2:
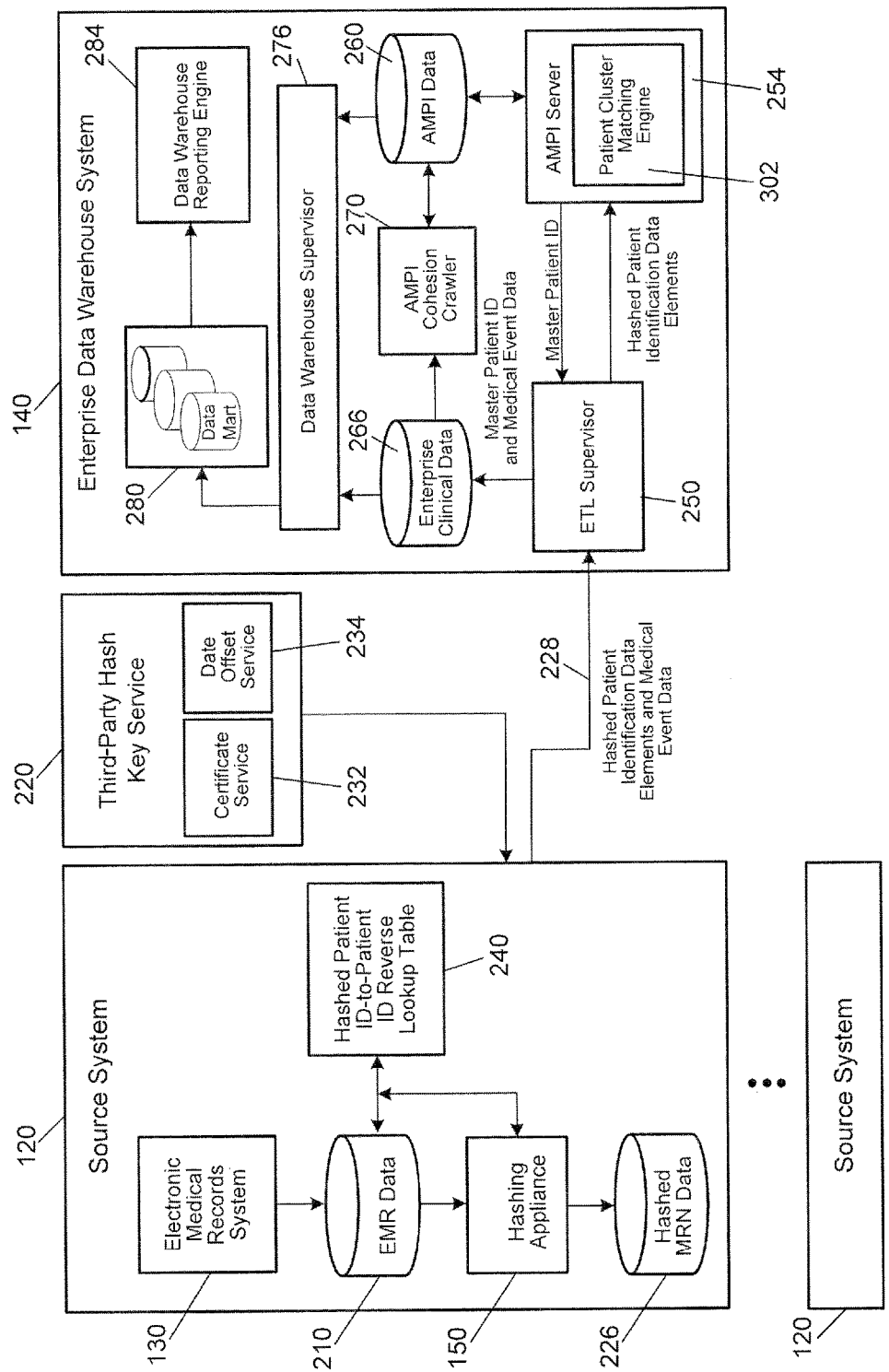
FIG. 2 is a block diagram of the environment of FIG. 1 in greater detail, according to a specific embodiment.

FIG. 2 shows the architectural environment 110 in greater detail. The architectural environment 110 in some embodiments may include a plurality of the source systems 120, which are frequently disparate and unrelated source systems. Such multiple source systems 120 may be associated with various providers, such as hospitals, medical offices, pharmacies, pathology providers, and the like. For a particular patient, it is often the case that the various providers do not share protected health information with other such providers, thus the protected health information or records may be maintained on separate, unrelated, and disparate computer systems.

As shown in FIG. 2, each source system 120 preferably includes the embedded hashing appliance 150. The source system 120 may include the electronic medical records system 130 coupled to an electronic medical records database 210 or data storage, either which may also be a remotely located component. The hashing appliance or component 150 receives input from the electronic medical records database 210 and receives hashing salt values and date offset values from a third-party hash key service 22. The hashing appliance 150 provides output to a hashed master record number database 226. As is understood in the art, a hash is the fixed-length resulting output of a cryptographic algorithm (such as SHA-1) that has been applied to an input data value. The practical effect of this function is to anonymize the input data value.

The hashing appliance 150 may provide output in the form of hashed data elements 228 to the enterprise data warehouse system 140 as part of an electronic medical record (EMR). The third-party hash key service 220 further includes a certificate service 232 and a data offset service 234. The source system 120 may also include a hashed system patient ID-to-patient ID reverse lookup table 240, which may be used to identify an actual patient based upon a request from the enterprise data warehouse system 140. The hashed system patient ID-to-patient ID reverse lookup table 240 may include the identity of the actual patient (unencrypted patient identifier) and a corresponding hashed value of the MRN, which was inserted into the record that was previously sent to the enterprise data warehouse system 140, as will be discussed below. The hashed system patient ID-to-patient ID reverse lookup table 240 may reside in or be operatively coupled to the EMR database 210, or may be included in or operatively coupled to the hashed MRN database 226.

The enterprise data warehouse system 140 may include an ETL (extract, transform, and load) supervisor 250, which receives hashed patient identification data elements from the anonymizing hashing appliance 150. The ETL supervisor 250 may be operatively coupled to an AMPI server (anonymized master patient index) 254. The AMPI server 254 is configured to store the encrypted and anonymized patient records in an AMPI data component 260 or memory storage, and its main function is to generate a single identifier that essentially aggregates all qualifying anonymized patient records so as to identify or map all such records to a single anonymous patient. Note that none of the data received from the hashing appliance 150 contains any confidential protected health information in readable or discernible form. All such data has been converted to a hash value, the contents of which cannot be decoded to arrive at the original value.

The ETL supervisor 250 may be operatively coupled to an enterprise clinical database 266, which in turn may receive input from an AMPI cohesion crawler 270, and may provide output to a data warehouse supervisor 276. The AMPI data storage 260 may be operatively coupled to the AMPI server 254, the AMPI cohesion crawler 270, and the data warehouse supervisor 276. In turn, the data warehouse supervisor 276 may be operatively coupled to a data mart 280, which may provide output to a data warehouse reporting engine 284.

Note that for any particular source system 120, all records of a particular patient will be assigned a unique master record number (MRN) by that source system. Thus, a particular source system 120 may supply to the hashing appliance 150, many records of a particular patient, which would all have the same MRN. Each record preferably includes a source identifier that identifies the source system that produced the record. Such a common MRN (at least from one source system 120) permits the records to be easily grouped together to reflect association with a single person.

However, when multiple source systems are involved, for example a first source system and a second source system, because the source systems may be separate and independent, the second source system may assign a totally new MRN to the same patient whose records also exist in the first source system, as neither source system is privy to the information contained in the other source system. Alternatively, the second source system may happen to assign the same MRN to a different person, thus two different persons may happen to have the same MRN because the first source system is completely separate and independent from the second source system. Also note that although the AMPI data may group all records associated with a single individual, those records may have a plurality of different MRNs because such MRNs were assigned by separate and independent source systems 120. Thus, an additional list or linked list may exist for each patient, which lists the various MRNs that may be associated with that patient. Essentially, the MRN for a particular patient may be considered to be an "alias" and such an alias may not be unique to that patient. The handling of ambiguity of in MRNs is discussed below with reference to FIG. 3.

With respect to FIG. 2, the enterprise clinical database 266 stores the anonymized electronic patient records received directly from each hashing appliance, while the AMPI data storage 260 stores the anonymized electronic patient records or at least those portions of the record that may be utilized to facilitate matching operations, and such records are associated with the specific source system that the MRN that the particular source system 120 may have assigned.

But as mentioned above, there may be some ambiguity associated with the MRN; thus, after all records have been processed by the AMPI cohesion crawler 270 and the patient cluster matching engine 302, each record is associated with a unique AMPI unifying number associated with a particular patient. Note that because each patient record includes the source identifier as well as the MRN, all records having the same MRN generated by one particular identified source system 120 correspond to the same patient. Conversely, two patient records having different MRNs generated by the same source systems 120 correspond to two different patients. However, two patient records having the same MRN generated by different source system 120 are ambiguous and are not definitive by themselves in identifying the patient. It may be also that the source identifier does not identify a particular source system 120, where multiple source systems 120 are aggregated and operated by the same healthcare provider or organization, and the same source identifier could be used to represent healthcare providers so long as MRNs were uniquely assigned within the universe of source systems 120 operated by that healthcare provider or organization.

The combination of the AMPI data component 260 and the enterprise clinical data component 266 may provide all of the relevant data. The data warehouse supervisor acts as an interface so that an entity that may employ or access the system 110 can obtain the appropriate records. The data mart 280 may represent the specific data of interest, which may be a reduced subset of the electronic medical records, and may omit data that is not of interest to the entity that may employ or access the system 110.

Note that only data elements corresponding to confidential protected health information of each patient health record are generally anonymized by the hashing appliance 150. If a data element is not confidential in nature nor could be used in any way to identify or help ascertain the identity of the patient, such data elements in the medical record may not be anonymized. Data elements containing confidential protected health information may include name, street address, zip code, date of birth, social security number, and the like. Dates of service are commonly recognized to be sensitive in nature (e.g., under HIPAA), but must be anonymized in a fashion that still permits mathematical comparisons to be conducted, as such information is necessary to permit useful analysis of the aggregated data. Conversely, data that need not be anonymized at all may include diagnosis information, test results, and the like.

As a general overview of the operation of the hashing appliance 150, a common salt value is used to create the hash corresponding to the each data element in the medical record containing confidential protected health information. If the same salt value and the same hash algorithm are used on the same data, such as a confidential patient data item, even if the data is culled from a different record or different source system, the ultimate hash value will be identical. In this way, data records corresponding to the same confidential protected health information can be aggregated because they should have a common hash value. Accordingly, each and every data element in the medical record corresponding to confidential protected health information is salted and hashed so as to render the confidential protected health information anonymous. The common salt value is obtained in a secure fashion (e.g., by exchange over a secure communications channel) from the third-party hash key service 220 so as to introduce a data element unknown to the enterprise data warehouse system 140 into the hashes. In this manner, the enterprise data warehouse system 140 (or entity employing the enterprise data warehouse system 140) cannot decode or "reverse engineer" the hashed data elements even if the enterprise data warehouse system 140 knows which hashing algorithm was used to create the hashes.

Given a sufficient number of records, correspondence or "agreement" among a plurality of different anonymized data elements permits a confidence level to be achieved that indicates that the disparate medical data records indeed correspond to the same patient, even though the identity of the patient, and/or the confidential patent information, is unknown. Moreover, such confidential protected health information will be anonymous because the hash value cannot be decoded or "reverse engineered" to provide the confidential protected health information. Accordingly, after a patient record has been anonymized, a particular patient record having openly available patient data can be provided to an entity, such as an aggregation entity, namely an enterprise data warehouse system 140 (or entity employing an enterprise data warehouse system 140) for use in research, diagnosis and the like, because each data element corresponding to confidential protected health information in the record has been anonymized and is represented only by the hash value.

The hashing appliance 150 may be a hardware or software component that resides within the firewall or other security measures of the data source system 120 or owner of the patient data records. The hashing appliance 150 appears as a black-box component that receives confidential protected health information fields of data records from the source system 120 and hashes each and every confidential protected health information field, and manages an offset for the date of service field so as to disguise the true date of service for that record. The date of service field in the record is preferably calculable and usable by the data aggregator or enterprise data warehouse system 140 and, thus, is preferably not fully anonymized because such dates are needed when performing analysis on the anonymized patient medical record. Thus, such dates of service are "disguised" with an offset value rather than being fully anonymized, thereby enabling evaluation of the timeliness of events relative to each other without disclosing the absolute date of the event.

The hashing appliance 150 also applies the common salt value received from the third-party hash key service 220 to create the hashed data for the confidential data elements. As alluded to above, because the hash was produced using a salt value, running a "brute force" decoding process, for example, using a name dictionary to decode every name to obtain the hash key, would not crack the hash code because the hash value is not a "direct hash" of the confidential data. Rather, the hash value is the result of a hash of confidential data plus a random value, for example, a random integer or string. After the hashing appliance 150 has anonymized each confidential field of data in the medical record, the record, including the anonymized data and the non-anonymized data, are encrypted and transmitted to the ETL supervisor 150 of the enterprise data warehouse system 140.

As discussed above, the hashing appliance 150 performs a hash on each confidential data field of each patient record. Further, each confidential data field is hashed twice. Preferably, a first hash is a 256-bit hash function, such as an SHA-256 (Secure Hash Algorithm) hash algorithm. The first hash is then hashed a second time to create the final hash value, and the first hash value is destroyed along with the confidential data field. The second hash value then replaces the confidential data in the record. Preferably, the second hash algorithm may be a 128-bit (or shorter) hash function, and preferably is a different type of hash algorithm compared to the first hash algorithm, such as an SHA-128 algorithm. Any suitable hash function may be used and the hash size may be 256 bits (SHA-256), 512 bits (SHA-512), or a different size. Note that because the second hash is a shorter hash than the first hash based on bit width, the second hash has lost data compared to the first hash. Because the first hash is destroyed and second hash is clearly missing information contained in the first hash, the hash cannot be decoded or reversed to obtain the original input to the first hash. The advantage of the smaller second hash is also that it takes less memory to store, increasing efficiency of the system 110.

Because the final hash value is a reduction hash, meaning a hash of a hash, and the first hash is destroyed along with the source confidential data, is it not possible for an attacker to associate the second hash value back to the original confidential data field. With respect to HIPAA, this process fully satisfies the applicable safe harbor rules for de-identification because the eventual hash is not derived from the confidential data field; rather, it is derived from an irreversible hash.

The hashing appliance 150 ultimately transmits the second and final hash value of the confidential data field as part of the data payload (which includes, non-confidential data of the patient record) to the enterprise data warehouse system 140. Note that because the confidential protected health information has been hashed and salted, and hashed a second time, anonymization of the confidential protected health information is irreversible. This means that neither the original owner of the data record residing on the source system 120 nor any component of the enterprise data warehouse 140 would be able to identify any of the confidential protected health information given the resulting anonymized data record, subject to one intentional process referred to as "re-identification" described below with respect to the source system 120.

The third-party hash key service 220 is preferably separate and independent from either the source system 120 or any components of the enterprise data warehouse system 140 so as to maintain a secure environment and prevent intentional or unintentional collaboration. Because no other components of the architectural environment 100 have access to the third-party hash key service 220, there is no possibility that the hash key can be decoded and reveal the confidential protected health information during the hashing process. The third-party hash key services 220 provides the common salt value and certificate service for data encryption to permit the hashing appliance 150 to create the hashed data elements.

In one embodiment, the third-party hash key services 220 derive the salt value from a radio frequency seed value to generate a truly random integer value. Alternatively, a string value may be derived from the radio frequency seed source. However, the common salt value is not necessarily limited to an integer value, an integer value of any particular length, or a string. The common salt value may also be a randomized string, a rational number, or any suitable value derived from any random source. Any suitable technique for generating the common salt value may be used, such as, for example, a UNIX-based OWASP function, and the like. Note that the same "salt" value should be used on corresponding encrypted fields in each data source.

Note that some known systems may include a trusted third party to handle the various data records and deal with security measures. However, the third-party hash key services 220 of embodiments of the system 110 is not a "trusted" third-party service. The third-party hash key services 220 is an independent component that supplies the common salt value and encryption support to two "untrusted" parties, namely the source system 120 and the enterprise data warehouse system 140, where neither component "trusts" the other component.

As mentioned above, the date offset service component 234 of the third-party hash key service 220 provides an offset or "disguise" for the date of service field of each patient record. The offset value is not saved back into the patient record but, rather, the hashing appliance 150 saves the offset value, which may correspond the each master record number in the source system 120 in which the hashing appliance 150 is embedded. Certain dates and, in particular, dates of service associated with the medical record of the patient are prohibited in a fully de-identified patient record that meets the HIPAA safe harbor requirements. To accommodate these requirements, it is necessary to offset the dates in such a way so that the date offset is unknown to the data receiver. In order to have consistency across all data aggregator, users of the system 100 that may receive usable data records from the enterprise data warehouse system 140, it is necessary to have consistency of the offset dates across all the data source systems 120. This allows calculations that are meaningful in data analysis without the use of actual dates. The following date offset method described below is consistent with those requirements.

In this process, the date is converted to an offset from a given base date, and the same base date is used for all data source systems 120. Thus, each date is merely an offset, for example, the value of −7, which corresponds to a date seven days prior to a base date. All dates, meaning the offset values, are relative to each other, which permits analysis of the data, such as population assessment and the like. In a first step to provide such date shifting, the date offset service 234 may generate a random number between 0 and −365. This implies that the range of dates would be limited to a one year time span, however, other values may be used so as to increase or decrease this time span. In other embodiments, a code for one of four seasons or quarters may be included to provide additional granularity. This integer value is then encrypted with a public key that the source system 120 provides to the hashing appliance 150. The hashing appliance 150 may receive the encrypted integer and associate this encrypted integer with the master record number (MRN) associated with this patient. Typically, this encrypted integer is defined and saved at the time the hashing appliance is installed in the source system 120.

Figure 3:
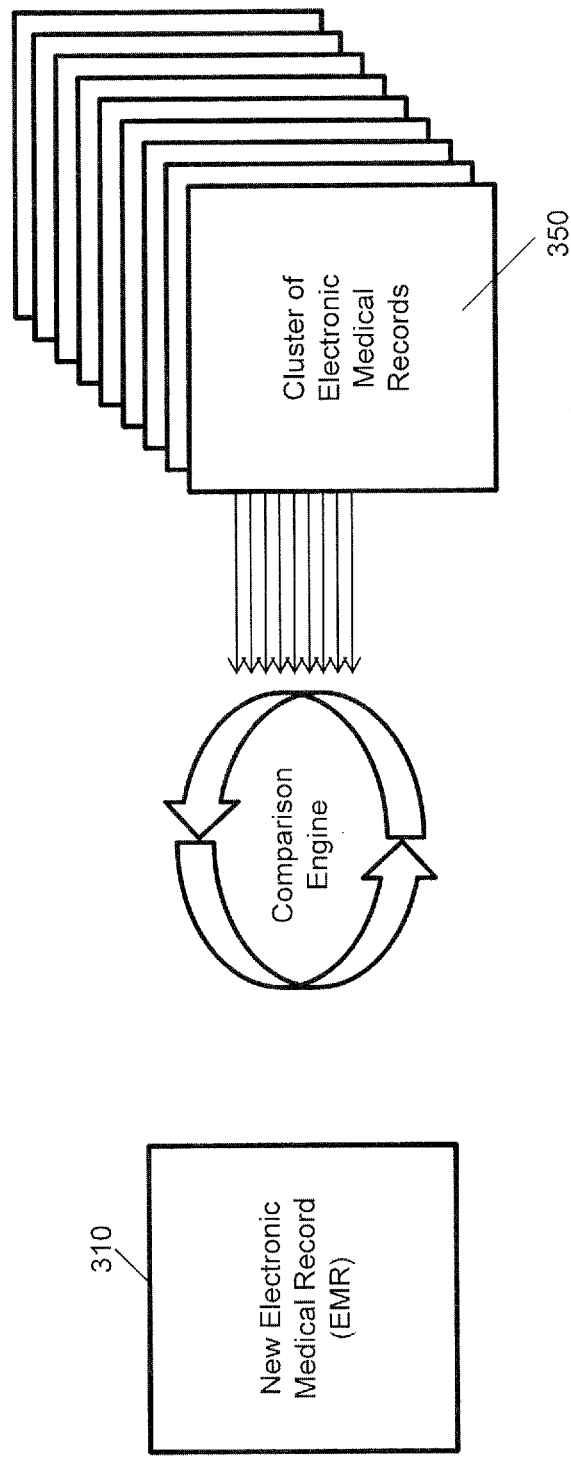
FIG. 3 is a pictorial diagram showing a comparison engine for matching data elements of a new electronic medical record to a cluster of medical records associated with the same patient.

FIG. 3 is a pictorial representations showing mapping of all medical fields in a new electronic medical record (EMR) 310 of one patient into a cluster of electronic medical records 350, all associated with that particular patient.

As described above with respect to the source system and corresponding MRNs, each electronic medical record includes a source identifier and record identifier or MRN, where the MRN is unique for all records coming from that source system 120. A mapping established between the source identifier and the MRN to a master record identifier, all subsequent instances of that MRN from that source system are mapped to the master record identifier and the contents of the elements are added to the valid values for each element in the master record. In one embodiment, the master record identifier and associated data are stored in the AMPI data component 260.

Further, as discussed above, the enterprise data warehouse 140 receives the anonymized patient records from the hashing appliance 150. Once received and stored by the AMPI server 254, the anonymized records should somehow be associated or mapped together to build the record base associated with a particular patient, although the patient identity is unknown. The final result of such associating or mapping is a single unique identifier that is able to tie together or aggregate all of the records common to one particular patient. This is based on the premise that identical confidential data elements that have been reduced to a hash value will necessarily have identical hash values, although irreversible and un-decodable.

For example, if one patient record having a hash value in the name field was derived and anonymized from a record having the name field of "Cecil Lynch," a second record obtained from the same or from a different source having that same hash value may be a good candidate to associate with the first record, where both records would be mapped to the same patient ("Cecil Lynch"). However, this is not necessarily the case, as there may be more than one patient having the name of Cecil Lynch. To determine if two such records are truly a match to the same patient, a patient cluster matching engine 302 is utilized to match newly received medical records with a cluster of medical records associated with the patient. The patient cluster matching engine 302 may be part of the part of the AMPI server or may be a separate and independent component thereof.

The patient cluster matching engine 302 attempts to map to a common patient all records that have a very high probability of corresponding to that patient. However, some data may be ambiguous, incomplete, or inaccurate. For example, a name in one record may be misspelled, or an abbreviation of the name may be used, and the like. Accordingly, identical hash values for name field may not be the same even though they actually correspond to the same patient. The converse may also be true. However, given a sufficient number of records for a particular patient, the AMPI cohesion crawler 270, in conjunction with the patient cluster matching engine 302, may be able to build a form of dictionary or variance dictionary to list and keep track of acceptable post-encrypted (post-hashed) data element values (variations) for each anonymized confidential data field.

FIG. 4 illustrates an exemplary rules table 400 that controls how the patient cluster matching engine 302 determines whether the field values of a newly received patient record should be clustered with those of one of the clusters of medical records stored in the AMPI database 260. Each row (405a-f) in the table defines a different combination of control values for controlling the operation of the patient cluster matching engine 302. Columns 2-14 (410a-n) of the table correspond to different fields of the medical record. For example, the fields may include an MRN number, which corresponds to the unique patient identifier assigned to a medical record by a specific source. The fields may also include other patient-related information such as the patient social security number, gender, year of birth, birth date, last name, first name, middle name, address, city, state, zip code, and phone number. Other fields associated with a patient medical may be included.

Each cell includes a control value utilized by the patient cluster matching engine 302 that specifies how that particular field is utilized by the patient cluster matching engine 302 in determining whether the hashed value associated with the field of the new medical record 310 should be clustered with a particular target cluster 350. For example, a control value of "1" may be used to indicate that the corresponding hash value associated with the field is required to be the same between the new medical record 310 and the target cluster 350 for there to be a match insofar as that hash value is concerned. The control value "0" may be used to indicate that the hash value associated with the field is required to be different between the new record and target cluster. A control value of "X" may be used to indicate a don't care condition. That is, whether the hash value associated with the field of the new record matches or does not match the corresponding hash value for the same field of the target cluster 350 is irrelevant. The control value "4" may be used to indicate that the hash value associated with the field is not specified in the new record or is not specified in the accumulated data for the patient. The control value "2" may be used to indicate an optional value and is used in conjunction with a count value 415. For example, referring to row seven, ten fields are set to the control value "2" and the count value is eight. This means that the hash values associated with eight or more of the ten fields must match between the new medical record 310 and the target cluster 350 for a match to exist. Other symbols, values, enumeration types, etc., may be utilized to represent the different match conditions.

In the exemplary rules table 400, the first rule 405a controls the patient cluster matching engine 302 to indicate a match when the MRN and the source of the new medical record 310 match those of a target cluster 350. The second rule 405b controls the patient cluster matching engine 302 to indicate a match when the social security number field in the new medical record 310 matches that of a target cluster 350. The third rule 405c controls the patient cluster matching engine 302 to indicate a mismatch when the gender, birth year, birthdate, last name, address, city, state, zip, and phone number fields of the new record match that of a target cluster 350, and the first and middle name fields do not match that same target cluster 350. This rule may be used to match newborn twins of the same gender who have not yet received a social security number. The fourth rule 405d controls the patient cluster matching engine 302 to indicate a mismatch when the gender field of the new medical record 310 does not match a target cluster 350. The fifth rule 405e controls the patient cluster matching engine 302 to indicate a match when the social security number field is not specified in new medical record 310, and the gender, birth year, birth date, last name, and first name fields match a target cluster 350. The sixth rule 405f controls the patient cluster matching engine 302 to indicate a match when the social security number field is not specified in the new medical record 310, but the gender field in the new medical record 310 matches that of a target cluster 350, and at least eight of the following fields match the target cluster 350: the birth year, birth date, last name, first name, middle name, address, city, state, zip, and phone fields.

In some implementations, the control values associated with the various fields in the rules table 400 may be specified manually. For example, it is reasonable to assume that the patient associated with a new record is the same patient associated with a target cluster when the MRN and source of the new medical record 310 match those of the target cluster 350. Therefore, the first rule 405a in the rules table 400 may be determined intuitively.

In addition or alternatively, the control values specified in the rules table 400 may be determined via a machine-learning algorithm. For example, a set of medical records from one or more sources for which the patients are known may be processed via, for example, a Monte Carlo analysis to determine the various combinations of hashed field values that result in a probability of a match or a mismatch. For example, the algorithm may determine that when the MRN for a new medical record 310 exists and the source is known, the new record is correctly matched to a target cluster 350 100% of the time. The algorithm may determine that when the hashed value of the social security number field for a new medical record 310 and a target cluster 350 match, the new medical record 310 is correctly identified as being associated with the target cluster 350 90% of the time. Similar relationships between the matching and mismatching of hashed field values in a new medical record 310 and a target cluster 350, and the percentage of time that the match of the new medical 310 record to the target cluster 350 is correct, may be determined via the analysis.

The probability of the correctness of a match or mismatch may determine placement of the determined rules in the rules table 400. For example, the rules may be ordered so that the rule resulting in the most correct match when the corresponding hash field values are available may be the first rule. The next rule may correspond to the rule that provides the next greatest correctness of a match when the corresponding hashed field values are available, and so on.

Figure 5:
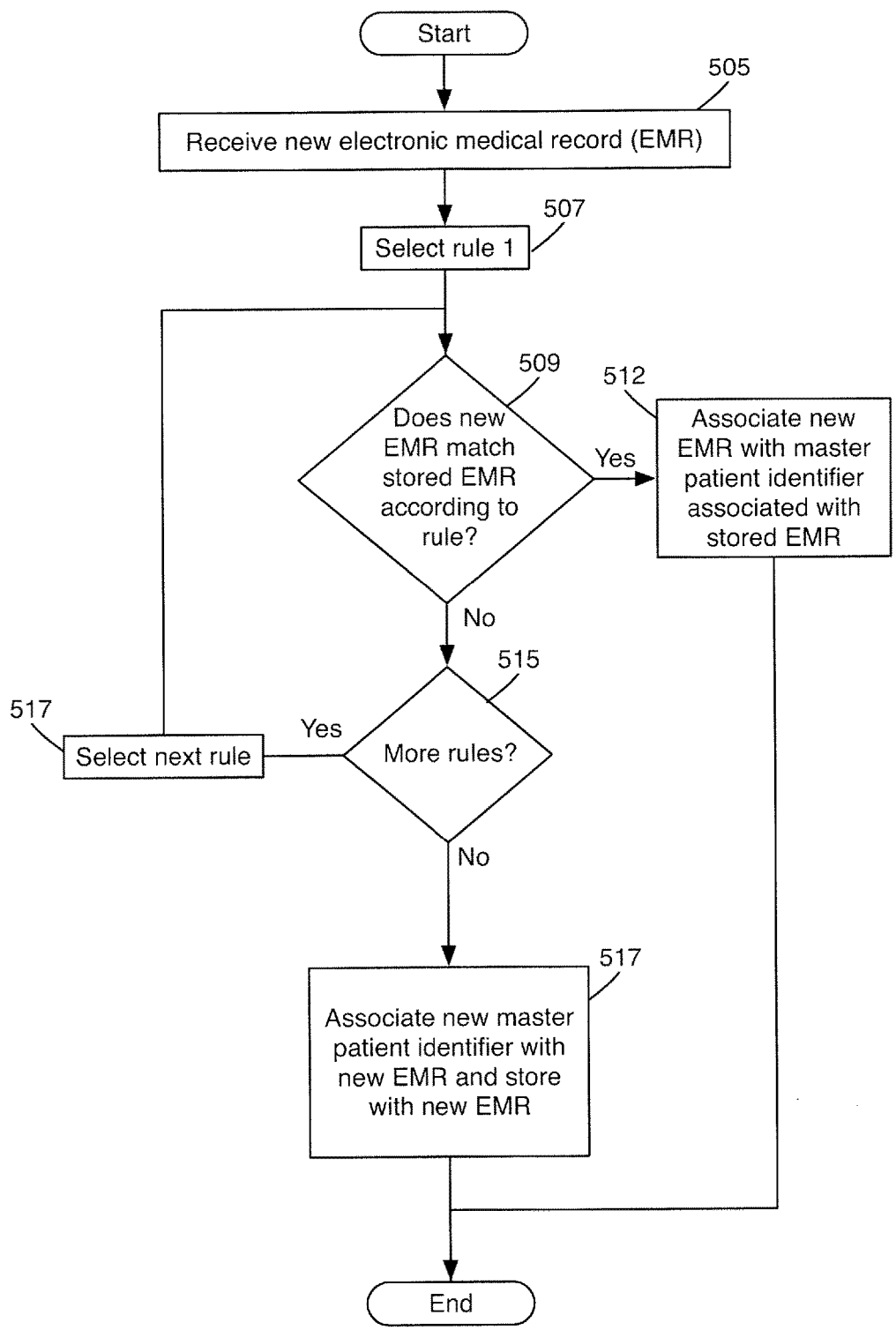
FIG. 5 is a flowchart that illustrations operations performed by the comparison engine.

FIG. 5 illustrates an exemplary group of operations that may be performed by the patient cluster matching engine 302 when determining whether a new medical record 310 is associated with a target cluster 350. The operations are described with reference to the rules table described in FIG. 4. In some implementations, the operations are specified in terms of instructions code stored in a non-transitory form of computer readable medium that is executed by the patient cluster matching engine for causing the patient cluster matching engine to perform the various operations.

At block 505, a new EMR may be received by the ETL supervisor 250 and stored to the enterprise clinical database 266.

At block 507, the first rule in the rules table 400 may be selected by the patient cluster matching engine 302.

At block 509, the control values associated with the fields of the selected rule may be utilized by the patient cluster matching engine 302 to determine whether the new medical record 310 matches a target cluster 350. For example, when operating according to the first rule 405a in the rules table 400, if the MRN field 410a and source are known for the new medical record 310, the patient cluster matching engine 302 may search for a target cluster associated with the same MRN field and source.

At block 512, if a match is found, the hash values associated with the fields of the new medical record 310 may be associated with the master patient identified associated with the matched target cluster 350.

If at block 509, the new medical record 310 is not found to match any target cluster based on the current rule, then at blocks 515 and 517, if there are additional rules in the rules table 400, the next rule is selected and the operations may repeat from block 509.

If at block 515, the new medical record 310 cannot be matched to any target cluster 350 according to any of the rules, then at block 517, a new cluster may be generated and populated with the hashed values of the fields of the new medical record 310, and the new target cluster may be assigned a unique AMPI unifying number/master patient identifier. The new cluster may then be stored to the enterprise clinical database 266.

As noted above, probability of the rules are arranged in the table according to the rules ability to accurately match a new record to a cluster, and the operations above apply the rules sequentially. It should be understood, however, that the rules in the table may be arranged differently and applied in a different order.

Figure 6:
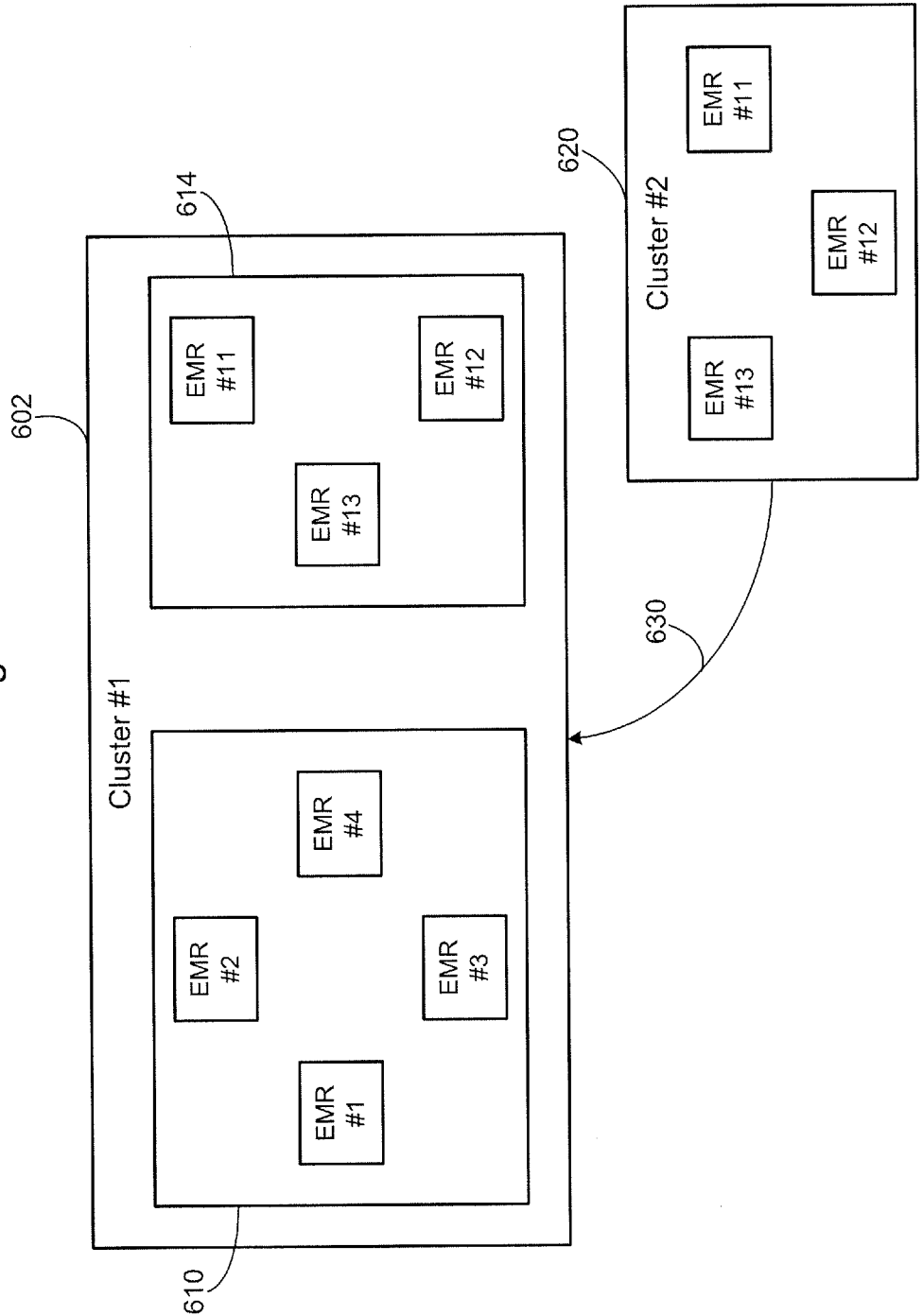
FIG. 6 is a diagram depicting a cohesion crawler process configured to join a new record to a target cluster.

Referring now to FIG. 6, an example of the process performed by the AMPI cohesion crawler 270 of FIG. 2 is shown, where two clusters are joined into a single cluster. The AMPI cohesion crawler 270 performs a continuous background process to inspect the data records as they are received so as to machine learn and link or map the various data records to common patients. As shown in this specific example, a cluster #1 602 includes electronic medical records nos. 1-4 (610) and electronic medical records 11-13 (614). Assume that the group of four EMRs (610) corresponds to a patient named George Smith. In this example, EMR #4 is a record from Nationwide Radiology and includes a hash of George's SSN while the other records do not.

Next, assume George Smith moves to a new city and is cared for by a new primary care physician. The new physician does not include George's SSN in his patient record. Worse still, the new physician switches George's first and middle names. Record EMR #13 is added that does not strongly connected to any existing cluster, so a new cluster is created 620 consisting only of the new EMR #13. In this example, another record (EMR #11) is added by a pharmacist for George that is most strongly connected to the record in the new cluster 620. However, it also does not include the hash of the SSN.

Assume that a record is now added by Nationwide Radiology using George's new address but also using his SSN. The cohesion crawler determines that the two records (EMR #11 and EMR #12) actually belong together because of the hash of the common SSN in each, thus joining all of George's records together notwithstanding instances of George's two addresses causing two subgroups. The records for EMR #11, EMR #12, and EMR#13 are now joined to the first cluster 602, as shown by line 630. Future records with either of George's addresses will be added to this cluster 602.

Figure 7:
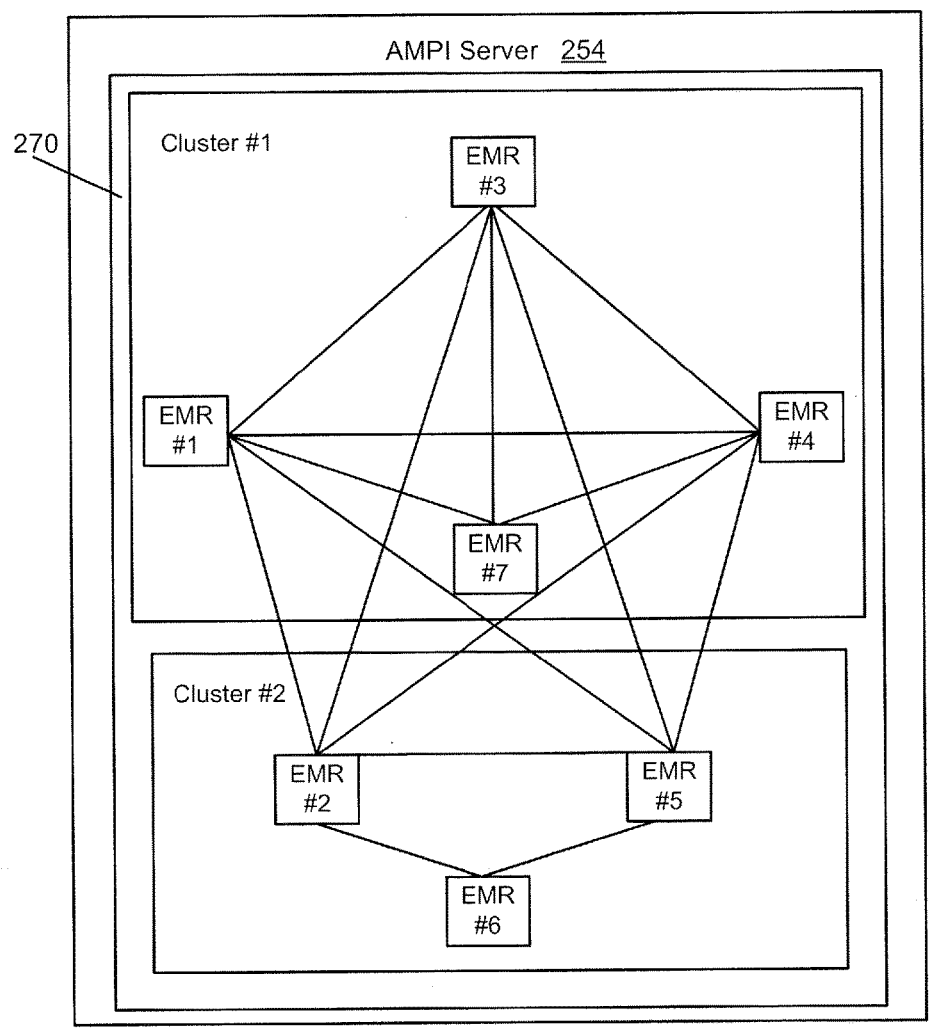
FIG. 7 is a diagram depicting a cohesion crawler process configured to split a single cluster into two clusters.

FIG. 7 is an example that depicts an "inverse" process performed by the AMPI cohesion crawler 270 to remedy a situation where EMRs were erroneously added to a target cluster, and shows a single cluster split into two separate clusters. In this example, twins named George Michael Foreman and George Thomas Foreman live at the same address and, except for their middle-name hashes, all hashes of identifying information possessed by the AMPI are the same. The twins are taken to an emergency room following an automobile accident. Social security numbers are collected for each twin. The hashes of the different SSNs combined with the hashes of the different middle names weaken the cohesion of the group such that it is recognizable that there are, in fact, two distinct groups with a single master patient identifier. Thus, there is an erroneous joining of EMRs in the cluster. The AMPI cohesion crawler 270 examines the group, recognizes that two distinct groups exist, and segregates them creating a new group for one of the twins.

Figure 8:
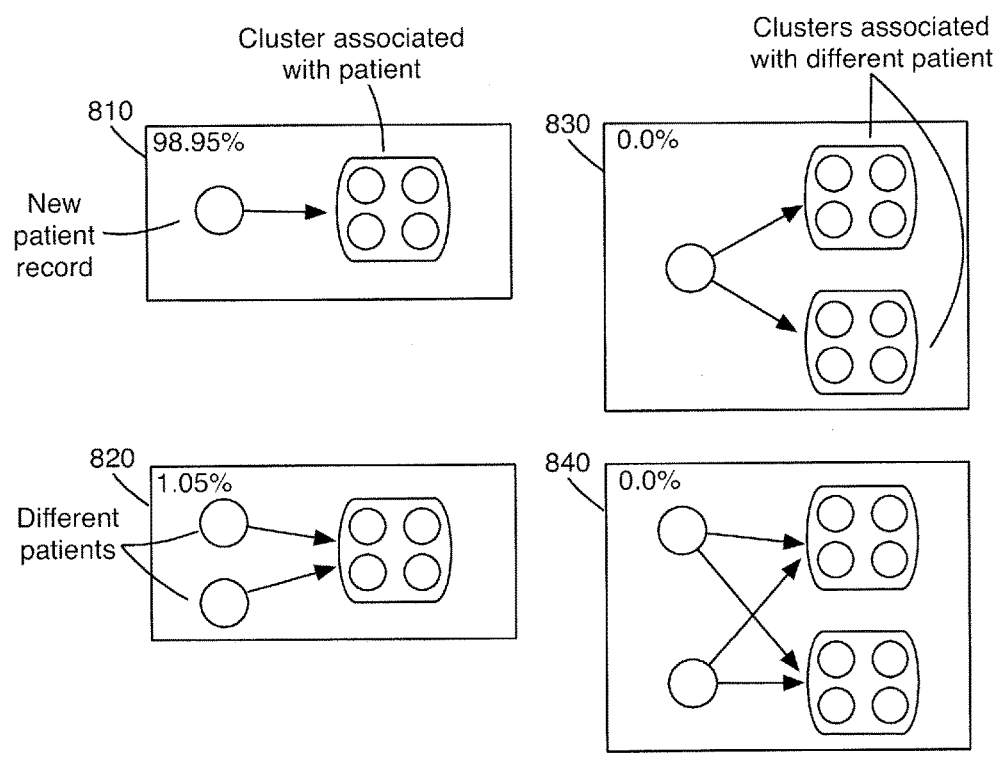
FIG. 8 shows empirical results of processing a plurality of patient records.

FIG. 8 is a diagram showing empirical test results for 30,000 test records processed by the system for anonymizing and aggregating patient records 110. The records are based on actual records with a representative sampling of common names, gender splits, age, demographics, and the like consistent with distributions and geographic definitions found in the United States. Further, certain of the records were edited to introduce typical errors or ambiguities in the data elements to test the efficacy of the system 110. For example, some records were edited to model typical demographic changes such as relocation, marriage/divorce, birth, etc. A first frame 810 shows about a 98.95% success rate where every record for a person is correctly linked to exactly one target cluster. A second frame 820 shows 1.05% occurrence of the data associated with a single patient being inadvertently split into two cluster. A third frame 840 shows a 0.0% occurrence rate of a second patient 842 being inadvertently included in the cluster associated with a different patient. A fourth frame 840 shows a 0.0% occurrence rate where two patients 852 are shown in two clusters.

Although the focus of the system of anonymizing and aggregating PHI 100 is to anonymize protected health information so that a patient cannot be identified from the aggregated data, there are certain situations when the patient should be identified or notified of certain medical conditions for their own health and safety. For example, an entity performing research based on the records provided by the system 100 may discover that certain bio-markers inspected may indicate that those persons may contract cancer. Thus, it is important that such individuals be contacted to inform them of the discovered risk. Because each patient record includes the MRN and the identifier of the source system that assigned that MRN, the source system 120 would be able to identify the actual patient associated with that MRN using the hashed system patient ID-to-patient ID reverse lookup table 240.

In one embodiment, when the hashing appliance 150 hashes the data field corresponding to the MRN, the data source 120 retains a table, such as the hashed system patient ID-to-patient ID reverse lookup table 240, which may associate the hashed MRN value with the true identity of the patient. This is referred to as re-identification. Preferably, the hashing appliance 150 performs only a single hash on the record indicator used for re-identification, rather than a double hash. When the patent should be notified due to a discovered health risk, the enterprise data warehouse system 140 may send back to the source system the encrypted and singly hashed MRN value of the record of the patient of interest.

Because the record or cluster of records of the patient to be contacted has a corresponding MRN that the source system 120 originally assigned, the source system 120 can decrypt the received MRN and look up the decrypted hash value in the hashed system patient ID-to-patient ID reverse lookup table 240, and ascertain the identity of the patient for purposes of notification. The system 100 and the source system 120 may encrypt the various hashed fields using known public key encryption methods.

Figure 9:
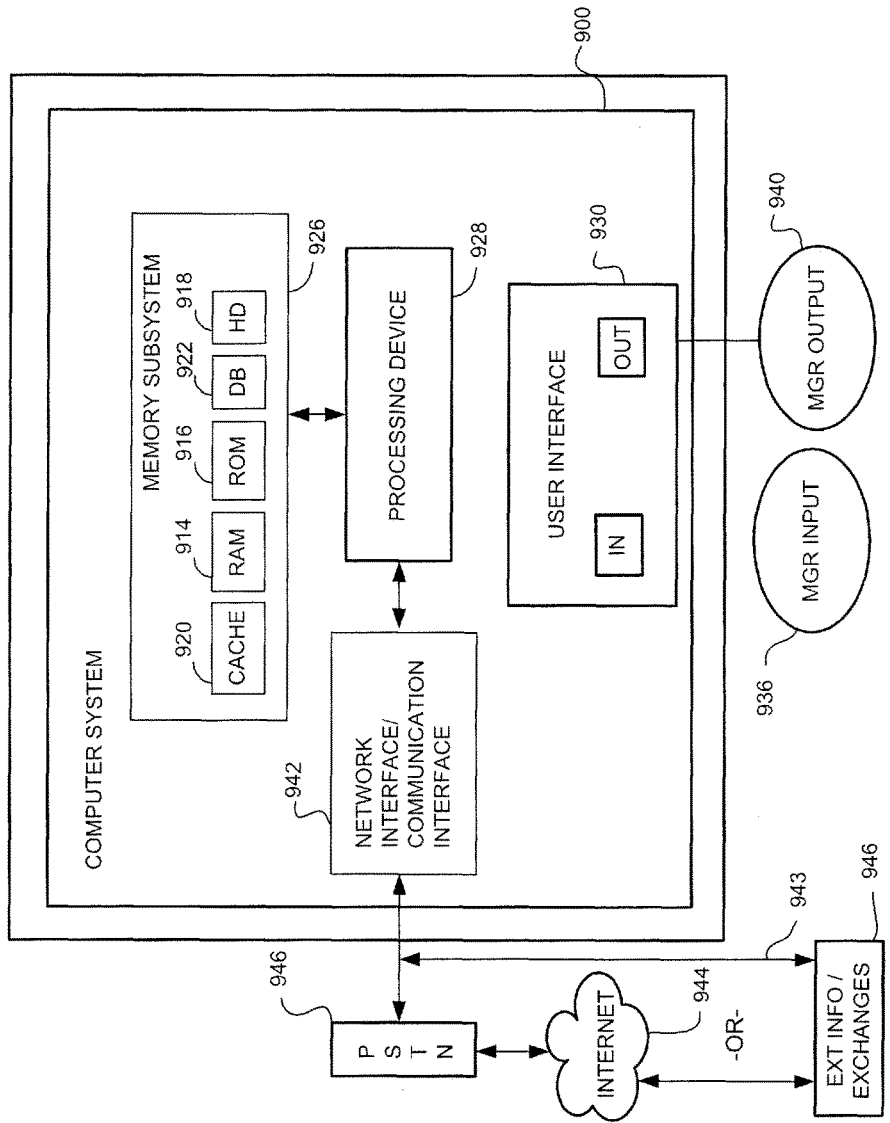
FIG. 9 is a representative computer system that may embody the system for anonymizing and aggregating protected health information, according to one embodiment.

FIG. 9 is a high-level hardware block diagram of a computer system 900, which may be part of the system for anonymizing and aggregating protected health information 110, or the system for anonymizing and aggregating protected health information 110 may be embodied as the computer system 900 cooperating with computer hardware components and/or as computer-implemented methods. The hashing appliance 150 may also be embodied in the computer system 900 as shown, with some variation. The system for anonymizing and aggregating protected health information 110 may include a plurality of software modules or subsystems operatively coupled to or residing in the computer system 900. The modules or subsystems, such as the hashing appliance 150, the third-party hash key service 220, the AMPI server 254, the AMPI cohesion crawler 270, and other components of the enterprise data warehouse system 140 may be implemented in hardware, software, firmware, or any combination of hardware, software, and firmware, and may or may not reside within a single physical or logical space. For example, the modules or subsystems referred to in this document and which may or may not be shown in the drawings may be remotely located from each other and may be coupled by a communication network.

The computer system 900 may be a personal computer, server, or other suitable computer, and may include various hardware components, such as RAM 914, ROM 916, hard disk storage 918, cache memory 920, database storage 922, and the like (also referred to as "memory subsystem 926"). The computer system 900 may include any suitable processing device 928, such as a computer, microprocessor, RISC processor (reduced instruction set computer), CISC processor (complex instruction set computer), mainframe computer, work station, single-chip computer, distributed processor, server, controller, micro-controller, discrete logic computer, and the like, as is known in the art. For example, the processing device 928 may be an Intel Pentium® microprocessor, x86 compatible microprocessor, or equivalent device, and may be incorporated into a server, a personal computer, or any suitable computing platform.

The memory subsystem 926 may include any suitable storage components, such as RAM, EPROM (electrically programmable ROM), flash memory, dynamic memory, static memory, FIFO (first-in, first-out) memory, LIFO (last-in, first-out) memory, circular memory, semiconductor memory, bubble memory, buffer memory, disk memory, optical memory, cache memory, and the like. Any suitable form of memory may be used, whether fixed storage on a magnetic medium, storage in a semiconductor device, or remote storage accessible through a communication link. A user or system manager interface 930 may be coupled to the computer system 900 and may include various input devices 936, such as switches selectable by the system manager and/or a keyboard. The user interface also may include suitable output devices 940, such as an LCD display, a CRT, various LED indicators, a printer, and/or a speech output device, as is known in the art.

To facilitate communication between the computer system 900 and external sources, a communication interface 942 may be operatively coupled to the computer system. The communication interface 942 may be, for example, a local area network, such as an Ethernet network, intranet, Internet, or other suitable network 944. The communication interface 942 may also be connected to a public switched telephone network (PSTN) 946 or POTS (plain old telephone system), which may facilitate communication via the Internet 944. Any suitable commercially available communication device or network may be used.

The logic, circuitry, and processing described above may be encoded or stored in a machine-readable or computer-readable medium such as a compact disc read only memory (CDROM), magnetic or optical disk, flash memory, random access memory (RAM) or read only memory (ROM), erasable programmable read only memory (EPROM) or other machine-readable medium as, for examples, instructions for execution by a processor, controller, or other processing device.

The medium may be implemented as any device that contains, stores, communicates, propagates, or transports executable instructions for use by or in connection with an instruction executable system, apparatus, or device. Alternatively or additionally, the logic may be implemented as analog or digital logic using hardware, such as one or more integrated circuits, or one or more processors executing instructions; or in software in an application programming interface (API) or in a Dynamic Link Library (DLL), functions available in a shared memory or defined as local or remote procedure calls; or as a combination of hardware and software.

In other implementations, the logic may be represented in a signal or a propagated-signal medium. For example, the instructions that implement the logic of any given program may take the form of an electronic, magnetic, optical, electromagnetic, infrared, or other type of signal. The systems described above may receive such a signal at a communication interface, such as an optical fiber interface, antenna, or other analog or digital signal interface, recover the instructions from the signal, store them in a machine-readable memory, and/or execute them with a processor.

The systems may include additional or different logic and may be implemented in many different ways. A processor may be implemented as a controller, microprocessor, microcontroller, application specific integrated circuit (ASIC), discrete logic, or a combination of other types of circuits or logic. Similarly, memories may be DRAM, SRAM, Flash, or other types of memory. Parameters (e.g., conditions and thresholds) and other data structures may be separately stored and managed, may be incorporated into a single memory or database, or may be logically and physically organized in many different ways. Programs and instructions may be parts of a single program, separate programs, or distributed across several memories and processors.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

We claim:

1. A system for anonymizing and aggregating protected information (PI) from a plurality of data sources, the system comprising:
 a master index server that communicates information to a data repository that includes a first processor coupled to non-transitory computer readable media that includes instruction code to cause the first processor to receive an anonymized record associated with an individual from a plurality of data hashing appliances and to store the received record to the data repository;
 a cluster matching engine that communicates information to the master index server and the data repository that includes a second processor coupled to non-transitory computer readable media that includes instruction code to cause the second processor to apply a plurality of rules to hashed data elements of the received anonymized record for comparing hashed data elements of the received anonymized record with hashed data elements of a plurality of clusters of anonymized records stored in the data repository, each record in a given cluster of anonymized records having been previously determined to be associated with a same individual and being associated with a unique cluster identifier, to determine whether the individual associated with the received anonymized record corresponds to an individual associated with one of the clusters of anonymized records; and
 when the received anonymized record is determined to correspond to the individual associated with one of the anonymized cluster of records stored in the data repository, the cluster matching engine is configured to add the received anonymized record to the one anonymized cluster of records associated with that individual,
 wherein the plurality of rules are listed in a rules table, and the rules are arranged based upon how accurately a given rule matches the received anonymized record to a correct cluster of anonymized records, wherein a first rule applied by the cluster matching engine corresponds to a rule that matches the received anonymized patient medical record to the correct cluster of anonymized records most accurately, and
 wherein the rules are applied sequentially until one of the rules matches the received anonymized record to the correct cluster of anonymized records.

2. The system according to claim 1, wherein each rule of the plurality of rules defines one or more control values that control how the cluster matching engine matches hashed data elements associated with different fields of the received anonymized record with hashed data elements associated with corresponding fields of the clusters of anonymized records.

3. The system according to claim 2, wherein the control values include a value that indicates that a hashed data element associated with a given field is required to be the same between the received anonymized record and a cluster of anonymized records for there to be a match, and a value that indicates that at least a specified number of hashed data elements associated with a plurality of different fields are required to be the same between the received anonymized record and the cluster of anonymized records for there to be a match.

4. The system according to claim 2, further comprising a rule generator configured to:
 receive a set of anonymized records from one or more sources for which an identity of individuals associated with the set anonymized records is known; and generate a plurality of different combination of control values and for each combination, determine an accuracy of the combination of control values in matching each record in the set to clusters of records associated with the same individual.

5. The system according to claim 1, wherein after the cluster matching engine adds the received anonymized record to the one anonymized cluster, the cluster matching engine is further configured to:
  determine whether the cluster is associated with more than one individual based on the plurality of rules; and
  if the cluster is determined to be associated with more than one individual, split the cluster into two or more clusters.

6. The system according to claim 1, wherein after the cluster matching engine adds the received anonymized record to the one anonymized cluster, the cluster matching engine is further configured to:
  compare data elements associated with each cluster with every other cluster based on the plurality of rules to determine whether the clusters are associated with a same individual; and
  when the clusters two or more clusters are determined to be associated with the same individual, combine the two or more clusters into one cluster.

7. The system according to claim 1, wherein each of the plurality of data hashing appliances is operatively coupled to a respective data source and is configured to receive from the respective data source one or more records associated with an individual, each record containing at least one data element corresponding to confidential protected information (PI), and a master record number (MRN) assigned by the respective data source, wherein each data hashing appliance is configured to:
  append a salt value to each data element corresponding to confidential PI in the patient medical record;
  generate a hash value for each data element corresponding to salted confidential PI;
  replace the data element corresponding to confidential PI with the corresponding generated hash value to generate an anonymized record.

8. The system according to claim 7, wherein a third-party hash key service provides the salt value to the hashing appliance, the third-party hash key service being separate and independent from the data source, the master index server, and the data repository.

9. The system according to claim 7, wherein the record associated with the individual includes data elements corresponding to confidential PI and non-confidential PI, wherein only data elements corresponding to confidential PI are anonymized at the respective data source prior to reception by the master index server.

10. The system according to claim 7, wherein:
  each data element corresponding to confidential PI is processed using a first hash algorithm to generate a first hash value;
  each first hash value is processed using a second hash algorithm to generate a second hash value;
  each first hash value is destroyed; and
  each data element corresponding to confidential PI in the record is replaced by the corresponding second hash value, such that the corresponding second hash value cannot be decoded so as to identify the value of the original data element corresponding to confidential PI.

11. The system according to claim 10, wherein the corresponding second hash values will be identical if the value of the original data element corresponding to confidential PI were identical.

12. A method for anonymizing and aggregating protected information (PI) from multiple data sources, the method comprising:
  receiving, by a master index server coupled to a data repository, an anonymized record associated with an individual from a plurality of data hashing appliances;
  applying, by a cluster matching engine operatively coupled to the master index server and the data repository, a plurality of rules to hashed data elements of the received anonymized record for comparing hashed data elements of the received anonymized record with hashed data elements of a plurality of clusters of anonymized records stored in the data repository, each record in a given cluster of anonymized records having been previously determined to be associated with a same individual and being associated with a unique cluster identifier, to determine whether the individual associated with the received anonymized record corresponds to an individual associated with one of the clusters of anonymized records;
  when the received anonymized record is determined to correspond to the individual associated with one of the anonymized cluster of records, adding the received anonymized record to the one anonymized cluster of records associated with that individual,
  wherein the plurality of rules are listed in a rules table, and the rules are arranged based upon how accurately a given rule matches the received anonymized record to a correct cluster of anonymized records, wherein a first rule applied by the cluster matching engine corresponds to a rule that matches the received anonymized patient medical record to the correct cluster of anonymized records most accurately, and
  wherein the rules are applied sequentially until one of the rules matches the received anonymized record to the correct cluster of anonymized records.

13. The method according to claim 12, wherein each rule of the plurality of rules defines one or more control values that control how the cluster matching engine matches hashed data elements associated with different fields of the received anonymized record with hashed data elements associated with corresponding fields of the clusters of anonymized records.

14. The method according to claim 13, wherein the control values include a value that indicates that a hash data element associated with a given field is required to be the same between the received anonymized record and a cluster of anonymized records for there to be a match, and a value that indicates that at least a specified number of hash data elements associated with a plurality of different fields are required to be the same between the received anonymized patient and the cluster of anonymized records for there to be a match y.

15. The method according to claim 12, wherein each of the plurality of data hashing appliances is operatively coupled to a respective data source and is configured to receive from the respective data source one or more records associated with individuals, each record containing at least one data element corresponding to confidential protected information (PI), and a master record number (MRN) assigned by the respective data source, wherein each data hashing appliance is configured to:

append a salt value to each data element corresponding to confidential PI in the patient medical record;

generate a hash value for each data element corresponding to salted confidential PI;

replace the data element corresponding to confidential PI with the corresponding generated hash value to generate an anonymized record.

16. The method according to claim 15, wherein a third-party hash key service provides the salt value to the hashing appliance, the third-party hash key service being separate and independent from the data source, the master index server, and the data repository.

17. The method according to claim 15, wherein the record associated with the individual includes data elements corresponding to confidential PI and non-confidential PI, wherein only data elements corresponding to confidential PI are anonymized at the respective data source prior to reception by the master index server.

18. A non-transitory computer readable medium having stored thereon instruction code for anonymizing and aggregating protected information (PI) from multiple data sources, the instruction code being executable by a machine for causing the machine to perform acts of:

receiving an anonymized record associated with an individual from a plurality of data hashing appliances;

applying a plurality of rules to hashed data elements of the received anonymized record for comparing hashed data elements of the received anonymized record with hashed data elements of a plurality of clusters of anonymized records stored in a data repository, each record in a given cluster of anonymized records having been previously determined to be associated with a same individual and being associated with a unique cluster identifier, to determine whether the individual associated with the received anonymized record corresponds to an individual associated with one of the clusters of anonymized records;

when the received anonymized record is determined to correspond to the individual associated with one of the anonymized cluster of records, adding the received anonymized record to the one anonymized cluster of records, wherein the plurality of rules are listed in a rules table, and the rules are arranged based upon how accurately a given rule matches the received anonymized record to a correct cluster of anonymized records, wherein a first rule applied by the cluster matching engine corresponds to a rule that matches the received anonymized patient medical record to the correct cluster of anonymized records most accurately, and wherein the rules are applied sequentially until one of the rules matches the received anonymized record to the correct cluster of anonymized records.

* * * * *